United States Patent
Czajka, Jr. et al.

(10) Patent No.: US 10,398,522 B2
(45) Date of Patent: *Sep. 3, 2019

(54) METHOD AND APPARATUS PERTAINING TO A MEDICAL DRAPE HAVING A SUCTION PORT

(71) Applicant: Medline Industries, Inc., Mundelein, IL (US)

(72) Inventors: Francis A. Czajka, Jr., Libertyville, IL (US); David Preskill, Highland Park, IL (US); Troy J. Lother, Kenosha, WI (US)

(73) Assignee: Medline Industries, Inc., Northfield, IL (US)

( * ) Notice: Subject to any disclaimer, the term of this patent is extended or adjusted under 35 U.S.C. 154(b) by 627 days.

This patent is subject to a terminal disclaimer.

(21) Appl. No.: 15/008,564

(22) Filed: Jan. 28, 2016

(65) Prior Publication Data

US 2016/0135915 A1 May 19, 2016

Related U.S. Application Data

(63) Continuation of application No. 13/339,837, filed on Dec. 29, 2011, now Pat. No. 9,278,166.
(Continued)

(51) Int. Cl.
*A61B 46/20* (2016.01)
*A61M 1/00* (2006.01)
(Continued)

(52) U.S. Cl.
CPC ............ *A61B 46/20* (2016.02); *A61B 46/00* (2016.02); *A61B 90/00* (2016.02); *A61B 90/04* (2016.02);
(Continued)

(58) Field of Classification Search
CPC ....... A61B 19/00; A61B 19/08; A61B 19/084; A61B 19/085; A61B 19/086;
(Continued)

(56) References Cited

U.S. PATENT DOCUMENTS 3,667,458 A 6/1972 Krebs
3,698,395 A 10/1972 Hasson
(Continued)

FOREIGN PATENT DOCUMENTS

CN 201602902 10/2010
CN 101496742 3/2011
(Continued)

OTHER PUBLICATIONS

Australian Patent Application No. 2012223335; Patent Examination Report No. 1; dated Aug. 14, 2015; 4 pages.
(Continued)

*Primary Examiner* — Tarla R Patel
(74) *Attorney, Agent, or Firm* — Fitch, Even, Tabin & Flannery LLP

(57) ABSTRACT

A medical drape has at least one suction port disposed. By one approach the medical drape includes a fenestration and the suction port is disposed within the fenestration. By one approach the fenestrated area includes an incise film (which may itself be fenestrated if desired) and the suction port is disposed through that incise film. Suction applied to this suction port facilitates maintaining the incise film in place on the patient. This suction port can have a first end configured to attach to suction tubing. The medical drape can include a patient-side spacer and this spacer can comprise a compressible, resilient material that is substantially permeable to liquids. If desired, such a spacer can be disposed over a patient-side suction opening of the suction port.

14 Claims, 8 Drawing Sheets

Related U.S. Application Data

(60) Provisional application No. 61/448,250, filed on Mar. 2, 2011.

(51) Int. Cl.
    *A61M 27/00*     (2006.01)
    *A61B 46/00*     (2016.01)
    *A61B 90/00*     (2016.01)
    *A61B 17/30*     (2006.01)
    *A61B 46/23*     (2016.01)

(52) U.S. Cl.
    CPC ............ *A61M 1/00* (2013.01); *A61M 1/0023* (2013.01); *A61M 1/0058* (2013.01); *A61M 1/0088* (2013.01); *A61M 27/00* (2013.01); *A61B 2017/306* (2013.01); *A61B 2046/205* (2016.02); *A61B 2046/236* (2016.02)

(58) Field of Classification Search
    CPC ... A61B 19/087; A61B 19/40; A61B 2217/00; A61B 2217/002; A61B 2217/005; A61B 46/20; A61B 90/00; A61B 46/00; A61B 90/04; A61B 2046/205; A61B 2046/236; A61B 2017/306; A61M 1/00; A61M 1/0023; A61M 1/0058; A61M 1/0088; A61M 27/00; A61F 5/37
    USPC ...... 128/846, 849–850, 853; 604/19, 27, 30, 604/35, 540, 541, 543
    See application file for complete search history.

(56) References Cited

U.S. PATENT DOCUMENTS

| | | |
|---|---|---|
| 3,707,964 A | 1/1973 | Patience et al. |
| 3,721,242 A | 3/1973 | Krusko |
| 3,750,664 A | 8/1973 | Collins |
| 3,763,857 A * | 10/1973 | Schrading .............. A61B 46/00 128/847 |
| 3,791,381 A | 2/1974 | Krzewinski |
| 3,799,161 A | 3/1974 | Collins |
| 3,826,253 A | 7/1974 | Larsh |
| 4,089,331 A | 5/1978 | Hartigan |
| 4,169,472 A | 10/1979 | Morris |
| 4,192,312 A | 3/1980 | Wilson |
| 4,205,668 A | 6/1980 | Criddle |
| D256,161 S | 7/1980 | Oliver |
| 4,384,573 A | 5/1983 | Elliott |
| 4,489,720 A | 12/1984 | Morris |
| 4,559,937 A | 12/1985 | Vinson |
| 4,586,498 A | 5/1986 | Morris |
| 4,616,642 A | 10/1986 | Martin |
| 4,798,201 A | 1/1989 | Rawlings |
| 4,869,271 A | 9/1989 | Idris |
| 4,890,628 A * | 1/1990 | Jackson ................ A61B 46/00 128/849 |
| 4,899,762 A | 2/1990 | Muller |
| 4,944,737 A | 7/1990 | Bloom |
| 5,042,507 A | 8/1991 | Dowdy |
| 5,060,662 A | 10/1991 | Farnsworth, III |
| 5,195,893 A | 3/1993 | Casale |
| 5,197,493 A | 3/1993 | Grier-Idris |
| 5,209,243 A | 5/1993 | Glassman |
| 5,345,946 A | 9/1994 | Butterworth |
| 5,380,278 A | 1/1995 | Mombrinie |
| 5,464,024 A | 11/1995 | Mills |
| D373,921 S | 9/1996 | Palomo |
| 5,778,889 A | 7/1998 | Jascomb |
| 5,778,890 A | 7/1998 | Lofgren |
| 5,800,483 A | 9/1998 | Vought |
| 5,803,086 A | 9/1998 | Scholz |
| 5,860,420 A | 1/1999 | Wiedner |
| 5,875,780 A | 3/1999 | Rodriguez |
| 5,991,666 A | 11/1999 | Vought |
| 6,007,564 A | 12/1999 | Haverstock |
| 6,019,102 A | 2/2000 | Becker |
| 6,032,670 A | 3/2000 | Miller |
| 6,199,553 B1 | 3/2001 | Hafer |
| 6,213,124 B1 | 4/2001 | Butterworth |
| 6,314,958 B1 | 11/2001 | Harroll |
| 6,345,621 B1 | 2/2002 | Chandler |
| D467,345 S | 12/2002 | Gingles |
| 6,497,233 B1 | 12/2002 | DeAngelis |
| 6,612,310 B2 | 9/2003 | Sklar |
| 6,694,981 B2 | 2/2004 | Gingles |
| 6,725,864 B2 | 4/2004 | Ewonce |
| 6,835,256 B2 | 12/2004 | Menzies |
| 6,843,252 B2 | 1/2005 | Harrison |
| 6,923,186 B2 | 8/2005 | Gavette |
| 6,966,320 B1 | 11/2005 | Baynes |
| 7,086,404 B2 | 8/2006 | Dusenbery |
| 7,588,034 B2 | 9/2009 | Mathis |
| 7,752,768 B2 | 7/2010 | Young |
| 7,853,311 B1 | 12/2010 | Webb |
| 8,011,371 B2 | 9/2011 | Rotolo |
| 8,079,365 B2 | 12/2011 | Block |
| 8,459,265 B2 | 6/2013 | Young |
| D693,603 S | 11/2013 | Esquivel |
| 8,721,629 B2 | 5/2014 | Hardman |
| 8,783,262 B2 | 7/2014 | Carrez |
| 8,967,150 B2 | 3/2015 | Carrez |
| 9,278,166 B2 | 3/2016 | Czajka, Jr. |
| 2001/0023697 A1 | 9/2001 | Hinley |
| 2002/0174870 A1 | 11/2002 | Ewonce |
| 2003/0051362 A1 | 3/2003 | Buckman |
| 2003/0159966 A1 | 8/2003 | McMichael |
| 2003/0187458 A1 | 10/2003 | Carlson |
| 2004/0103903 A1 | 6/2004 | Falahee |
| 2004/0118049 A1 | 6/2004 | Chen |
| 2004/0118409 A1 | 6/2004 | Griesbach |
| 2005/0234322 A1 | 10/2005 | Lober |
| 2006/0207609 A1 | 9/2006 | Gil |
| 2006/0219249 A1 | 10/2006 | Czajka |
| 2008/0006279 A1 | 1/2008 | Bodenham |
| 2009/0158487 A1 | 6/2009 | Paulsen |
| 2009/0277460 A1 | 11/2009 | Carrez |
| 2010/0192960 A1 | 8/2010 | Rotolo |
| 2010/0263678 A1 * | 10/2010 | Baumann ................ A61F 7/02 128/849 |
| 2011/0015557 A1 | 1/2011 | Aali |
| 2011/0030702 A1 | 2/2011 | Czajka, Jr. |
| 2011/0041995 A1 | 2/2011 | Adams |
| 2011/0126845 A1 * | 6/2011 | Hoffmann ............... A61F 13/51 128/849 |
| 2011/0214679 A1 | 9/2011 | Chua |
| 2011/0247634 A1 | 10/2011 | Young |
| 2012/0017921 A1 | 1/2012 | Esquivel |
| 2012/0222686 A1 | 9/2012 | Lockwood |
| 2012/0222687 A1 | 9/2012 | Czajka |
| 2012/0298115 A1 | 11/2012 | Haines |
| 2013/0284187 A1 | 10/2013 | Esquivel |
| 2013/0304080 A1 | 11/2013 | Landry |
| 2014/0012119 A1 | 1/2014 | Geaghan |
| 2014/0261457 A1 | 9/2014 | Lother |
| 2015/0135398 A1 | 5/2015 | Czajka |
| 2015/0359596 A1 | 12/2015 | Jarrelle |
| 2016/0135915 A1 | 5/2016 | Czajka, Jr. |
| 2017/0258543 A1 | 9/2017 | Chua |

FOREIGN PATENT DOCUMENTS

| | | |
|---|---|---|
| EP | 2151211 | 2/2010 |
| SU | 445412 | 10/1974 |
| WO | 9510986 | 4/1995 |
| WO | 2006094062 | 9/2006 |
| WO | 2011088326 | 7/2011 |
| WO | 2012078620 | 6/2012 |
| WO | 2013036387 | 3/2013 |

(56) References Cited

FOREIGN PATENT DOCUMENTS

| WO | 2014083573 | 6/2014 |
|----|------------|--------|
| WO | 2015191953 | 12/2015 |

OTHER PUBLICATIONS

Canadian Patent Application No. 2,832,104; Office Action dated Aug. 12, 2015; 5 pages.
Chinese Patent Application No. 2012800215110; Office Action dated Mar. 20, 2015 with English translation.
Chinese Patent Application No. 2012800215110; Office Action dated Nov. 4, 2015 with English translation.
Extended European Search Report from European Application No. 12751757.1 dated Aug. 12, 2014.
International Search Report and Written Opinion; PCT Patent Application No. PCT/US2014/023215; dated Jul. 24, 2014.
Notification of the First Office Action dated Mar. 20, 2015 from Chinese Patent Application No. 2012800215110.
PCT, Notification Concerning Transmittal of International Preliminary Report on Patentability, in International Application No. PCT/US2012/27284, dated Sep. 12, 2013.
PCT, Notification of Transmittal of the International Search Report and the Written Opinion of the International Searching Authority, or the Declaration, in International Application No. PCT/US12/27284, dated Jun. 29, 2012.
International Search Report and Written Opinion from PCT/US2017/022278 dated Jun. 19, 2017; 11 pages.
International Search Report and Written Opinion from PCT/US2017/022450 dated Jun. 7, 2017; 12 pages.
Extended European Search Report from European Patent Application No. 17173255.5 dated Aug. 18, 2017; 10 pages.
Article 94(3) EPC from European Patent Application No. 12751757.1 dated Jan. 5, 2017; 7 pages.
Australian Patent Application No. 2012223335; Patent Examination Report No. 2; dated Aug. 15, 2016; 6 pages.
European Extended Search Report for European Application No. 18200143 dated Mar. 29, 2019.

\* cited by examiner

METHOD AND APPARATUS PERTAINING TO A MEDICAL DRAPE HAVING A SUCTION PORT

RELATED APPLICATIONS

This application is a continuation of U.S. application Ser. No. 13/339,837, filed Dec. 29, 2011, which claims the benefit of U.S. application Ser. No. 61/448,250, filed Mar. 2, 2011. The contents of these applications are incorporated herein by reference in their entireties.

TECHNICAL FIELD

This invention relates to medical drapes, and more particularly to a medical drape used in connection with surgical or medical procedures.

BACKGROUND

Medical drapes are widely used to cover a patient during the performance of surgical and other medical procedures as a protective measure. Medical drapes are typically made sterile and aid in preventing the transmission of infection(s) to the patient by helping create a sterile environment surrounding the surgical site and maintaining an effective barrier that reduces the passage of microorganisms between non-sterile and sterile areas.

These drapes often include fenestrations that extend completely through the drape to provide access to a corresponding area of the patient's body over which the respective fenestration lies. In many cases an incise film fills all or a portion of the fenestrated area. This incise film will often have a side that includes an adhesive to facilitate adhering the incise film to the patient's skin to help retain the installed position of the incise film. That said, it is not uncommon for an adhesively-bonded incise film to nevertheless change position during use due to any number of contributing factors As but one small example in these regards, surgical procedures often permit a patient's bodily fluids to escape the body (via, for example, a surgical incision within the fenestration). Unfortunately, such fluids can negatively impact the adhesive bond between the aforementioned incise film and the patient.

BRIEF DESCRIPTION OF THE DRAWINGS

The above needs are at least partially met through provision of the method and apparatus pertaining to a medical drape having a suction port described in the following detailed description, particularly when studied in conjunction with the drawings, wherein.

Figure 1:
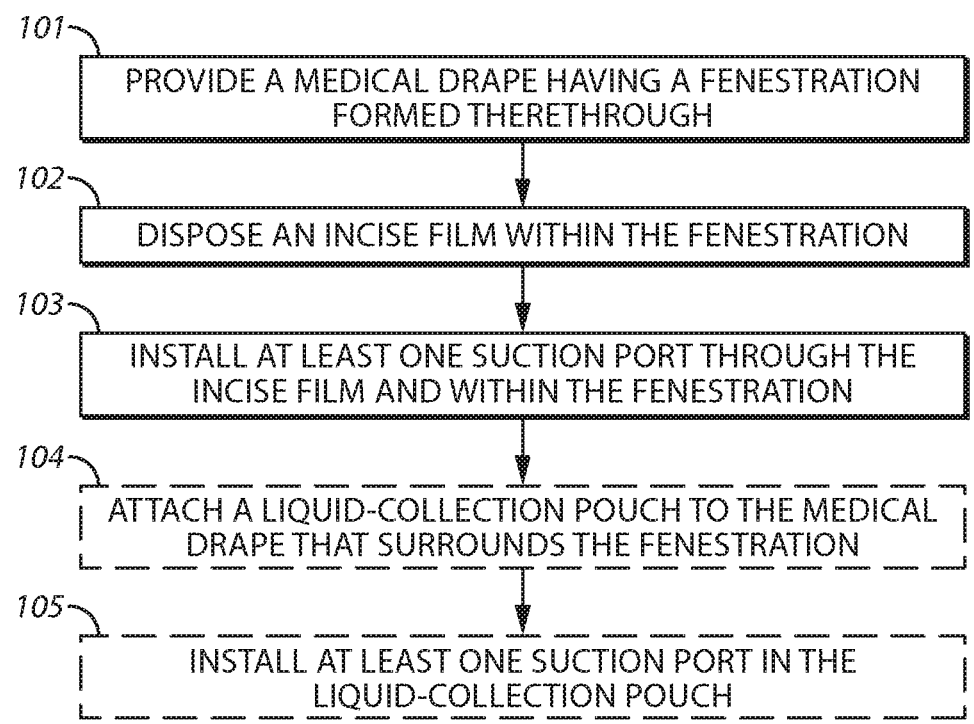
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a fenestrated medical drape has at least one suction port disposed within the fenestrated area. By one approach the medical drape comprises a fenestrated medical drape. In such a case the suction port can be disposed wholly or partially within the fenestrated area or adjacent the fenestrated area as desired. By one approach the fenestrated area includes an incise film (which may itself be fenestrated if desired) and the suction port is disposed through that incise film. So configured, suction applied to this suction port facilitates maintaining the incise film in place on the patient.

This suction port can have a first end configured to attach to suction tubing. An opposing end of the suction port can have one or more laterally-disposed suction openings configured to be disposed essentially adjacent a patient's skin when the medical drape is operationally disposed on the patient. These laterally-disposed suction openings may, by one approach, be radially disposed with respect to a central pneumatic pathway that pneumatically connects, for example, to the aforementioned first end of the suction port.

These teachings will accommodate having more than one such suction port within the medical drape's fenestration. This can permit the user to select a particular suction port to employ during a given procedure. Or, if desired, this will facilitate simultaneously using two or more of the suction ports during the procedure.

These approaches are highly flexible in practice. For example, the foregoing approaches can be employed in conjunction with a pouch that is disposed about the fenestration to collect at least some of the patient's exuding liquids. This pouch can itself include another suction port that serves to facilitate removing at least some of the liquids from within the pouch.

So configured, these teachings are readily employed to leverage the efficacy of existing medical drapes and particularly fenestrated medical drapes having an incise film disposed within the fenestration. The suction introduced between the patient's skin and the incise film serves to help maintain the positioning of the incise film to either supplement the aforementioned adhesive or to serve in lieu thereof. These teachings can be economically deployed and can greatly aid in maintaining the operational integrity of the procedure field.

These and other benefits may become clearer upon making a thorough review and study of the following detailed description. Referring now to the drawings, and in particular to FIG. 1, an illustrative process 100 that is compatible with many of these teachings will now be presented.

Figure 2:
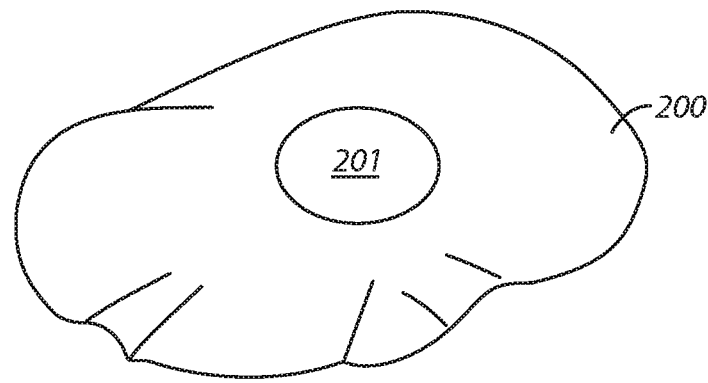
FIG. 2 comprises a perspective view as configured in accordance with various embodiments of the invention.

At step 101 this process 100 provides a medical drape having a fenestration formed therethrough (it being understood that these teachings are not limited to fenestrated medical drapes). FIG. 2 provides an illustrative example in these regards. The drape 200 generally comprises a main portion having a front side that faces away from a patient (not shown) when operationally deployed and a back side that faces towards (and typically at least partially contacts) the patient when so deployed. Such a drape 200 can be at least largely comprised of a water-repellent or water-impermeable material and/or is coated with such a water-repellent or water impermeable material to prevent the passage of bodily fluids and/or contaminating microorganisms. For example, the main portion may be made of various woven, non-woven, and/or hydroentangled materials. The base fabrics used to comprise the drape 200 may include Airlaid, spunlace, spunbound, meltblow, and blends of polyester, polypropylene, and polyethylene as desired, alone or in various layered combinations.

The fenestration 201 comprises an opening formed in the drape 200 having a shape, size, and location suitable to the intended use of the drape 200. These teachings will readily accommodate having a plurality of such fenestrations of identical or differing sizes and shapes as desired. Such a fenestration 201 permits a surgical or other medical procedure to be performed therethrough. Though such a fenestration 201 can have essentially any shape, in many cases such fenestrations are generally egg-shaped though oval shapes, pear shapes, and football shapes (i.e, American football) are also sometimes employed.

Figure 3:
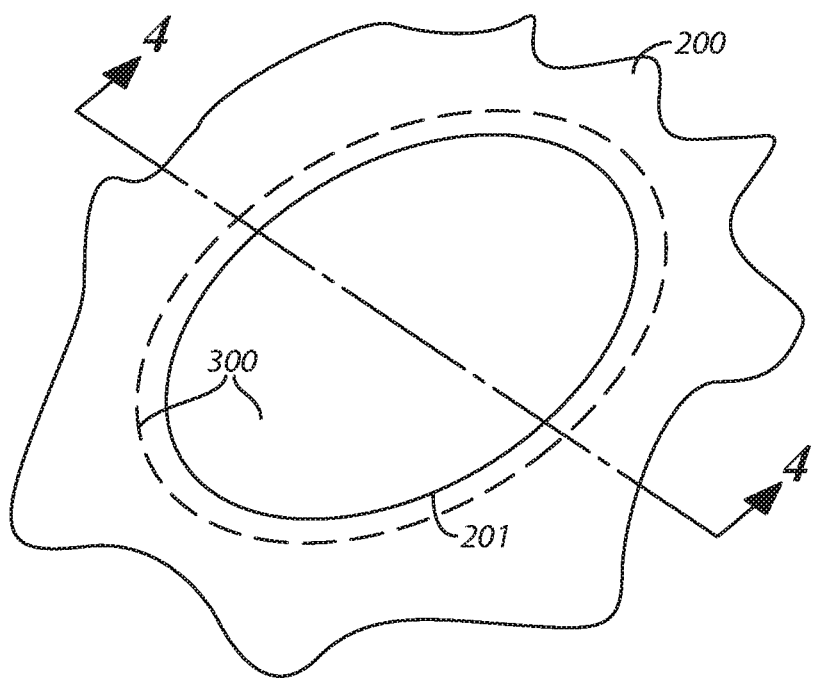
FIG. 3 comprises a perspective detail view as configured in accordance with various embodiments of the invention.
Figure 4:
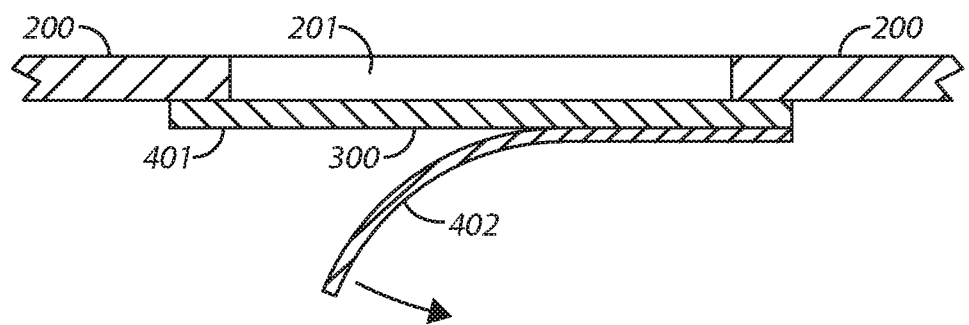
FIG. 4 comprises a side-elevational sectioned view as configured in accordance with various embodiments of the invention.

Referring again to FIG. 1, at step 102 this process 100 provides for disposing an incise film within the fenestration 201. FIGS. 3 and 4 offer an illustrative example in these regards. In this particular example the incise film 300 completely fills the fenestration 201. The edges of the incise film 300 in fact extend a bit beyond the fenestration's boundary to provide material to facilitate connecting the incise film 300 to the drape 200.

The composition of such an incise film 300 is well known to those skilled in the art of medical drapes. The incise film 300 may be generally transparent to facilitate convenient use by the medical-services provider. In many cases the material will be both resilient yet pliable to thereby facilitate the ease by which the drape 200 in general and the incise film 300 in particular can be placed in a deployed and conformal disposition on a patient.

The incise film 300 can be secured to the drape 200 using any of a variety of attachment mechanisms. Examples include, but are not limited to, adhesives, thread (or the like), ultrasonic welding, and so forth. As the present teachings are not particularly sensitive to choices made in these regards, further elaboration will not be provided here.

By one approach, and referring now in particular to FIG. 4, the incise film 300 has an adhesive 401 disposed on one side thereof. In many cases this side will comprise the patient side of the incise film 300 when the drape is operationally deployed. This adhesive will facilitate retaining the incise film 300 (and, at least to some extent, the drape 300 as well) in an operationally-deployed state by adhering to the patient's skin (not shown). When using an adhesive 401 these teachings will also accommodate using a peel patch 402 in combination therewith. Peel patches are generally known in the art and often comprise a treated paper or plastic sheet that is loosely retained in position by the adhesive 401 but that can also be readily removed (for example, by peeling the peel patch 402 away from the adhesive 401) to thereby expose the adhesive 401 at a time of need.

Figure 5:
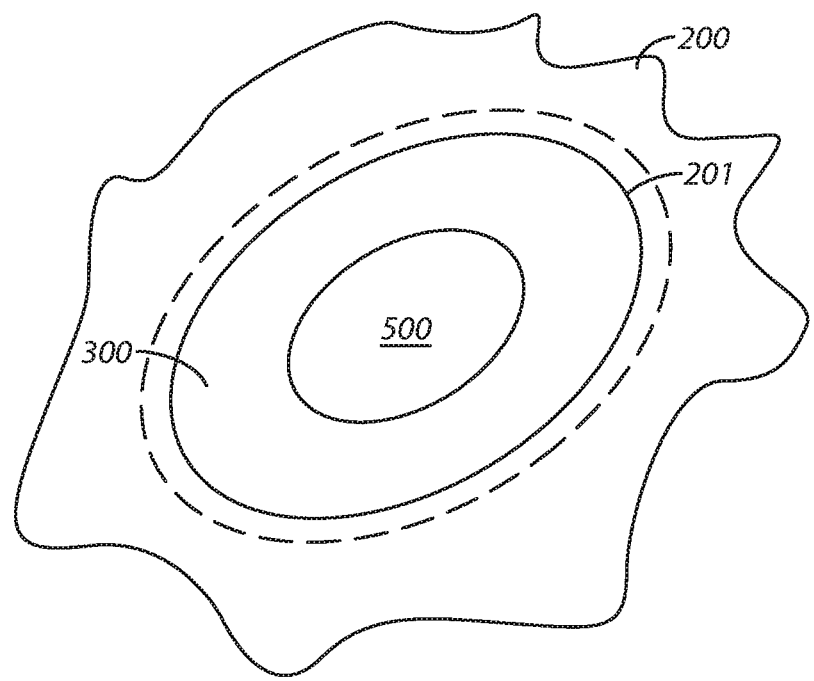
FIG. 5 comprises a perspective detail view as configured in accordance with various embodiments of the invention.

In some cases, and as illustrated in FIG. 3, the incise film 300 is whole; i.e., there are no openings of any kind that penetrate through the incise film 300. In other cases, the incise film 300 will comprise a pre-fenestrated incise film 300. FIG. 5 depicts a simple example in these regards and illustrates a pre-fenestrated incise film 300 having a single fenestration 500 formed therethrough prior to deployment and use. When using a non-pre-fenestrated incise film 300 such as the one illustrated in FIG. 3, of course, the surgeon will often form an opening through the incise film 300 (using, for example, a scalpel) during the course of the corresponding surgical/medical procedure.

Referring again to FIG. 1, step 103 of this process 100 then provides for installing at least one suction port through the incise film 300 and within the fenestration 201. This reference to a "suction port" will be understood to refer to a component that is not, for example, a mere opening through the incise film 300 (such as, for example, the fenestration 500 depicted in FIG. 5). Instead, a suction port will be understood to comprise a component configured and designed to couple (in a sealed manner) to a suction tube or the like such as one typically finds in a hospital operating room to permit suction provided by the suction tube to be delivered to a suction input portion of the suction port. More particularly, it will be understood that a "suction port" will not collapse or deform during ordinary use as an element in a pneumatic pathway that delivers suction.

Figure 6:
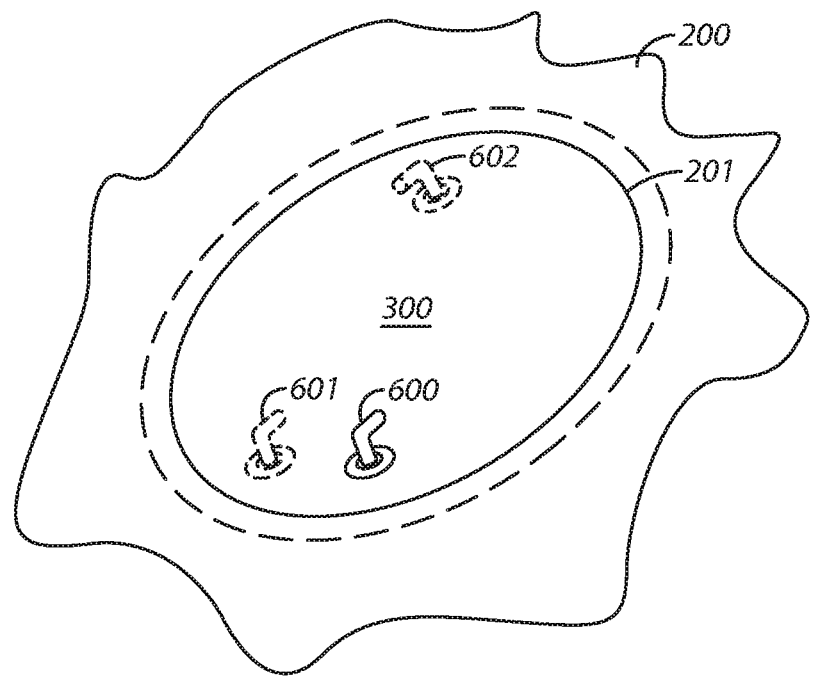
FIG. 6 comprises a perspective detail view as configured in accordance with various embodiments of the invention.

FIG. 6 provides an illustrative example in these regards. In this example the suction port 600 is disposed within the fenestration 201 of the drape 200 and, more particularly, is also disposed through the incise film 300. (If desired, one or more of these suction ports 600 can be disposed only partially within the fenestrated area or even outside the fenestrated area and adjacent the fenestrated area.) By one approach only one such suction port serves in these regards. By another approach, however, additional such suction ports (such as those denoted by reference numerals 601 and 602) can also be provided. Providing a plurality of suction ports can permit the medical-services provider to select a particular suction port (or ports) to use that will best accommodate the circumstances that attend a particular medical procedure. These teachings will also accommodate, if desired, providing suction ports having differing suction-tube interfaces to accommodate a range of different suction tube sizes and configurations.

These teachings will accommodate a wide variety of differently-configured suction ports 600. By one approach, for example, the suction port can comprise a simple short tube. By another approach the suction port 600 can comprise a pneumatic pathway having one or more bends, twists, turns, or the like.

Figure 7:
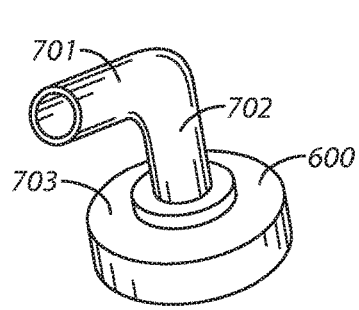
FIG. 7 comprises a perspective view as configured in accordance with various embodiments of the invention.

FIG. 7, for example, depicts one approach in these regards. Here, the suction port 600 comprises an elbow-shaped component having a first portion 701 that is generally perpendicular to a second portion 702 that is itself generally perpendicular to a base 703. In this example these various components of the suction port 600 share a common pneumatic pathway that passes therethrough. The aforementioned first portion 701 comprises a first end of the suction port 600 and is configured to attach in a sealed manner to suction tubing (not shown). (These teachings will also accommodate, if desired, a suction port 600 that comprises a T-shaped component to thereby provide an exposed suction coupling to use with ancillary equipment such as, for example, a yankauer, a vacuum-relief valve, or the like.)

Figure 8:
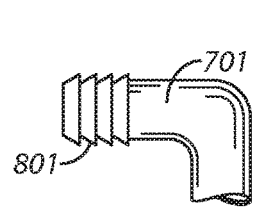
FIG. 8 comprises a side-elevational detail view as configured in accordance with various embodiments of the invention.

In this particular illustrative example this first end has a smooth, regular exterior surface (where the exterior surface can be tubular in shape as illustrated or inwardly inclined to form a cone to facilitate easier insertion of this first portion 701 into the tip of a length of suction tubing). Numerous possibilities exist in these regards, however. For example, as shown in FIG. 8, this first portion 701 can have a plurality of small truncated cones 801 to facilitate suction tube insertion and retention. In the examples shown the suction tubing remains in place through frictional interaction with the first portion 701 of the suction port 600. These teachings will work with other approaches, however, including threaded connections, snap-based connections, and so forth as desired.

Figure 9:
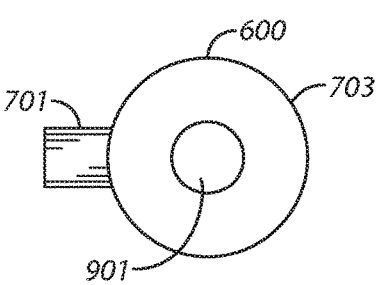
FIG. 9 comprises a bottom plan view as configured in accordance with various embodiments of the invention.

FIG. 9 illustrates that the suction port 600 can have a suction-input opening(s) 901 on the underside of the aforementioned base 703. This suction-input opening 901, of course, pneumatically couples to and comprises a part of the aforementioned common pneumatic pathway. Such a suction-input opening 901 will tend to face the patient's skin when the drape 200 is operationally disposed on the patient.

Figure 10:
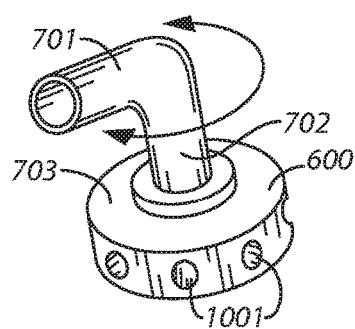
FIG. 10 comprises a perspective view as configured in accordance with various embodiments of the invention.

These teachings will accommodate a variety of approaches with respect to the location, orientation, and/or number of suction-input openings. By way of illustration, and referring now to FIG. 10, the suction port 600 can include one or more laterally-disposed suction-input openings 1001 in addition to, or in lieu of, the aforementioned patient-facing suction-input opening 901. In the specific example shown there are a plurality of these laterally-disposed suction-input openings 1001 and these pathways are radially disposed with respect to a central pneumatic pathway (i.e., the aforementioned common pneumatic pathway) like the spokes of a wheel. Such laterally-disposed suction-input openings 1001 will tend to present themselves laterally with respect to the patient's skin when the drape 200 is operationally disposed on the patient.

By one approach these various parts of the suction port 600 can comprise an integral whole. (As used herein, this reference to "integral" will be understood to refer to a combination and joinder that is sufficiently complete so as to consider the combined elements to be as one. Accordingly, two items would not be considered "integral" with respect to one another if they are merely connected to one another by the action of a holding member such as a screw, bolt, clamp, clip, or the like.)

These teachings will support other approaches in these regards, however. As one illustrative example, the elbow-shaped portion (comprising the first and second portions 701 and 702) can be physically discrete with respect to the base 703. In such a case, if desired, the elbow-shaped portion may be configured to, for example, rotate with respect to the base 703 (as suggested by the curved arrow in FIG. 10). This rotational capability can facilitate conveniently positioning the suction tubing as desired.

The suction port 600 can be comprised of such materials as may best suit a particular intended application setting. This can include, for example, any of a variety of metals or plastics. For many purposes, as when the suction port 600 comprises a uni-piece embodiment, a generally-resilient but mildly-pliable and non-brittle plastic material will serve well in these regards.

Figure 11:
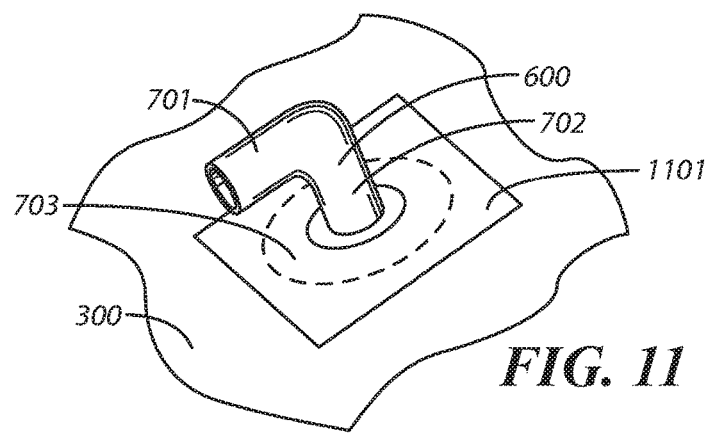
FIG. 11 comprises a perspective detail view as configured in accordance with various embodiments of the invention.

As described above, the suction port 600 is disposed within the drape's fenestration 201. When the fenestration 201 includes an incise film 300, the suction port 600 will typically also pass through and be supported by that incise film 300. Referring to FIG. 11, by one approach this can comprise using a small patch 1101 having a hole to accommodate, here, the elbow-shaped portion of the suction port 600 but not the base 703 thereof. This patch 1101 can have an adhesive surface that adheres to the incise film 300 to thereby hold the suction port 600 in place. These teachings will accommodate, however, essentially any useful manner of maintaining the respective position of the suction port 600 with respect to the fenestration 201.

Figure 12:
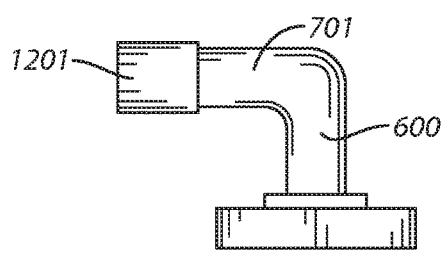
FIG. 12 comprises a side-elevational view as configured in accordance with various embodiments of the invention FIG. 13 comprises a side-elevational detail view as configured in accordance with various embodiments of the invention.

Referring to FIG. 12, a removable cap 1201 can serve to seal the suction port 300 if desired. Such a cap 1201 can be useful, for example, when providing a plurality of suction ports with a given drape 200. In such a case, such caps 1201 will serve to seal suction ports that the medical-services provider may choose to not use during the medical procedure. By one approach, for example, such a cap 1201 can remain in place via a friction fit. For ease of use this friction fit can be sufficiently weak to permit removal of the cap 1201 by hand.

Figure 13:
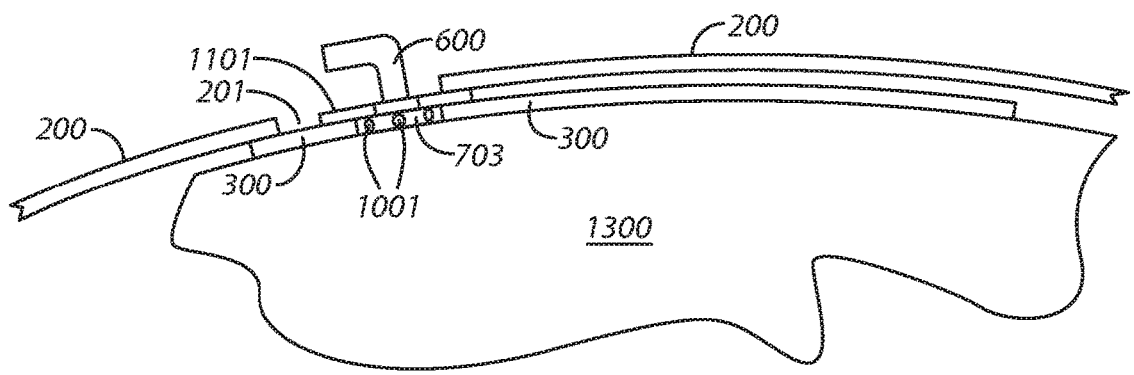

So configured, and referring now to FIG. 13, the drape 200 can be placed over (all or part) of a patient's body 1300 such that the fenestration 201 is disposed over the area of interest. The aforementioned peel patch 402 can be removed by hand and the incise film 300 placed into contact with the patient's body 1300. A suction tube (not shown) can then be attached to the suction port 600 and suction applied to draw in air via the suction-input openings 1001 in the base 703 of the suction port 600 and also through the patient-facing opening 901 which does not appear in this view).

Generally speaking, though some amount of liquid (such as blood or other bodily fluids from the patient) may enter the suction port 600 and exit via the suction tubing, the primary purpose of this arrangement is to pull at least a partial vacuum between at least portions of the incise film 300 and the skin of the patient to thereby aid in retaining the placement of the incise film 300 on the patient 1300 and thereby supplement the aforementioned adhesive 401 (when present).

These teachings provide for only modest, inexpensive alterations of existing drape designs and the use of suction capabilities that are typically already available in a medical-services venue. Accordingly, the incremental costs of adopting and utilizing these teachings are virtually nil. The benefits, however, can be considerable. Imposing a vacuum between the incise film 300 and the patient's skin can greatly improve the opportunities for the aforementioned adhesive to successfully hold the incise film 300 in place during a medical procedure. This, in turn, can improve sterility conditions for the patient and reduce the overall time required to complete the medical procedure.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

Figure 14:
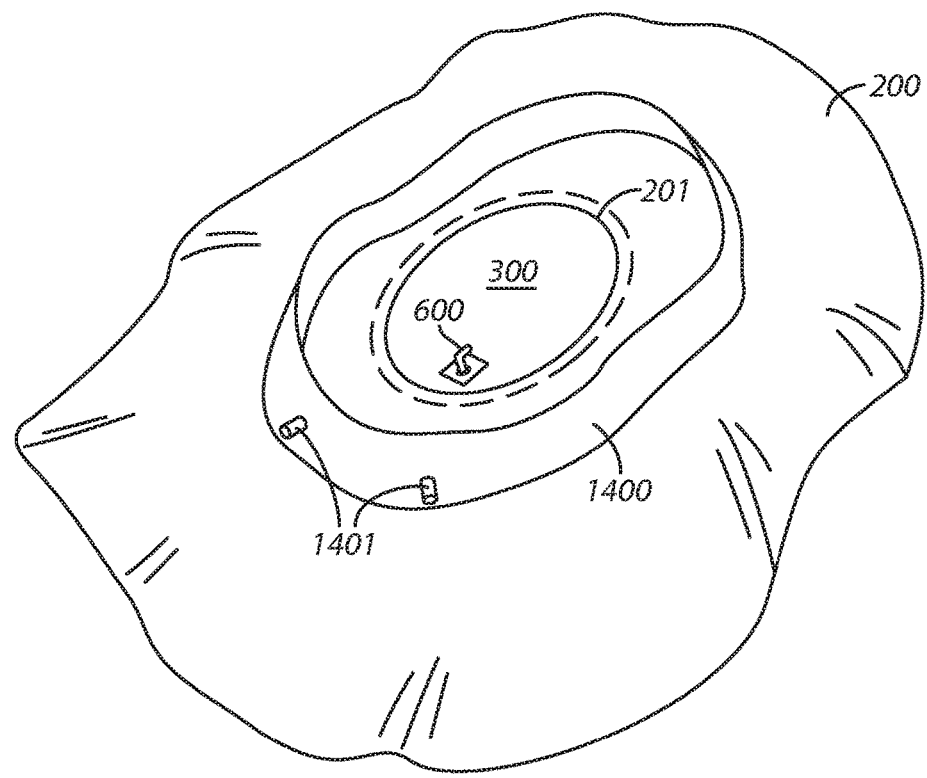
FIG. 14 comprises a perspective view as configured in accordance with various embodiments of the invention.

As but one illustrative example in these regards, and referring to FIGS. 1 and 14, at optional step 104 the aforementioned process 100 provides for attaching a liquid-collection pouch 1400 to the medical drape 200. This liquid-collection pouch 1400 surrounds the drape's fenestration 201 and can be comprised of a material similar or identical to the drape 200. So configured, fluids exuding from the patient from within the fenestration 201 can flow outwardly from the fenestration and pool within the liquid-collection pouch 1400. In such a case, and again as desired, optional step 105 provides for installing at least one suction port 1401 in (i.e., through) the liquid-collection pouch 1400. This suction port 1401 can connect to corresponding suction tubing and thereby remove at least some liquid as may have been retained by the liquid-collection pouch 1400. If desired, the same source of suction as one employs for the suction port 600 that is disposed within the drape's fenestration 201 can also be employed to provide suction to the liquid-collection pouch's suction port 1401.

Figure 15:
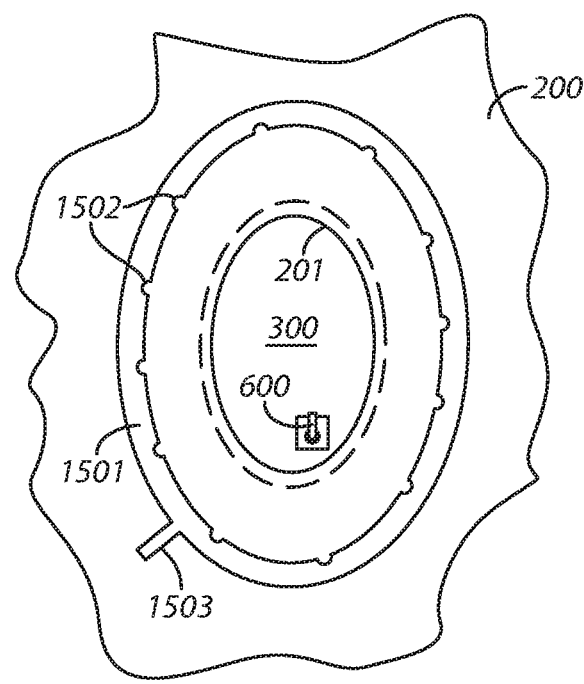
FIG. 15 comprises a top plan view as configured in accordance with various embodiments of the invention.

In such a case, and referring now to FIG. 15, the liquid-collection pouch's suction port can comprise a plurality of suction ports 1502 that substantially surround the medical drape's fenestration 201. By one approach, and as illustrated, these suction ports 1502 can comprise openings in tubing 1501 that surrounds (or at least substantially surrounds) the drape's fenestration 201 and that includes an exit port 1503 that can connect, for example, to suction tubing.

Figure 16:
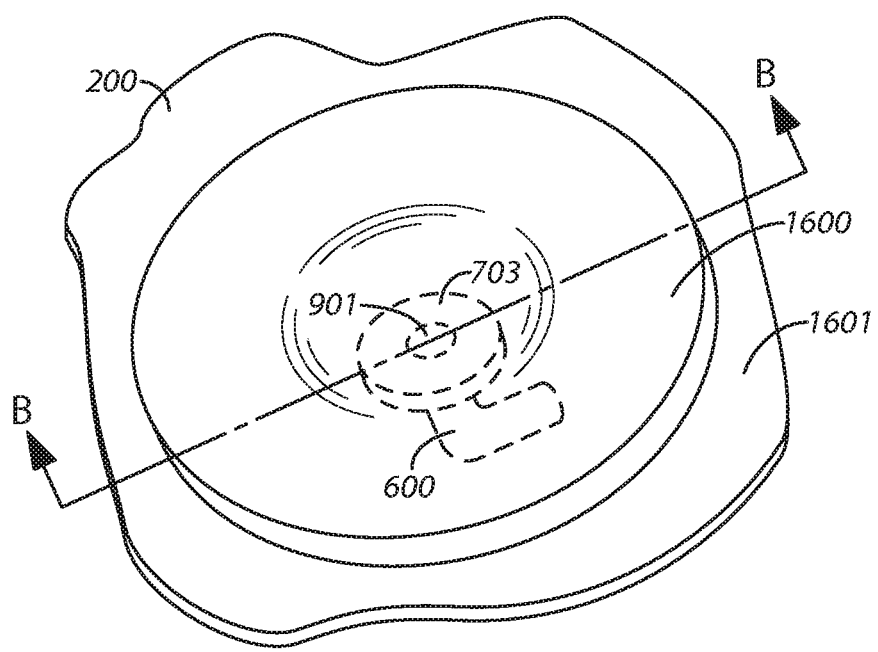
FIG. 16 comprises a perspective detail view as configured in accordance with various embodiments of the invention.
Figure 17:
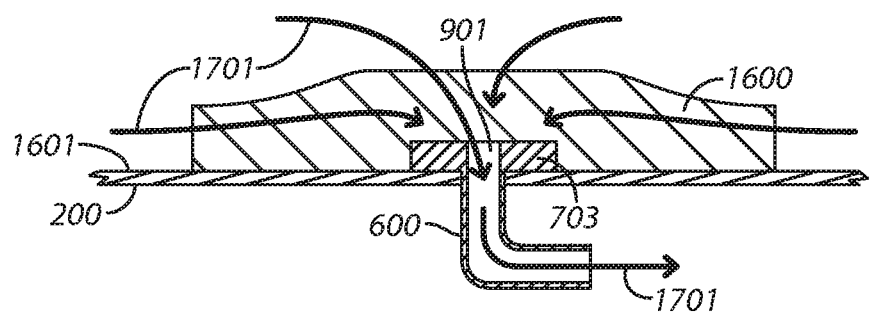
FIG. 17 comprises a side-elevational sectioned view along line B-B from FIG. 16.

As another example in these regards, and referring now to FIGS. 16 and 17, a spacer 1600 can be employed in conjunction with these teachings. This spacer 1600 can be disposed, for example, on a patient side 1601 of the medical drape 200. By one approach, the spacer 1600 can be attached to the patient side 1601 of the medical drape 200 using an adhesive of choice.

In this illustrative example the spacer 1600 is disposed over the suction opening 901 of the suction port 600. This spacer 1600 can be comprised of a compressible, resilient material such as any of a variety of sponge-like materials. In addition (or in lieu thereof) this spacer 1600 can comprise a liquid-permeable spacer such that bodily fluids 1701 can readily flow substantially unimpeded therethrough and hence into and through the suction port 600 as illustrated in FIG. 17.

So configured, the medical drape 200 can be disposed over the patient. When suction is applied via the suction port 600, air and liquids are sucked through the spacer 1600 and the suction port 600 to thereby create at least a partial vacuum between at least portions of the medical drape 200 and the patient's body to thereby assist in maintaining the medical drape 200 in place even in the absence of an adhesive.

Figure 18:
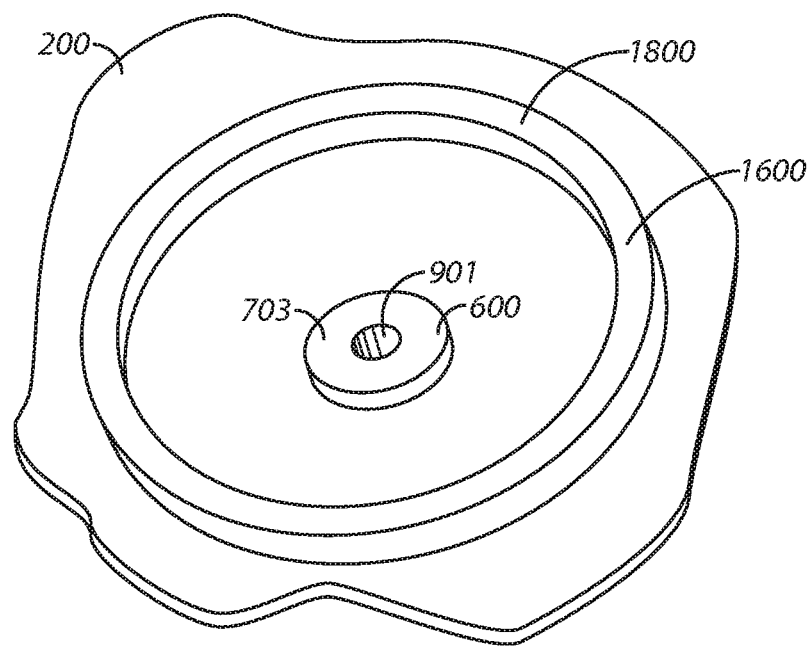
FIG. 18 comprises a perspective detail view as configured in accordance with various embodiments of the invention.
Figure 19:
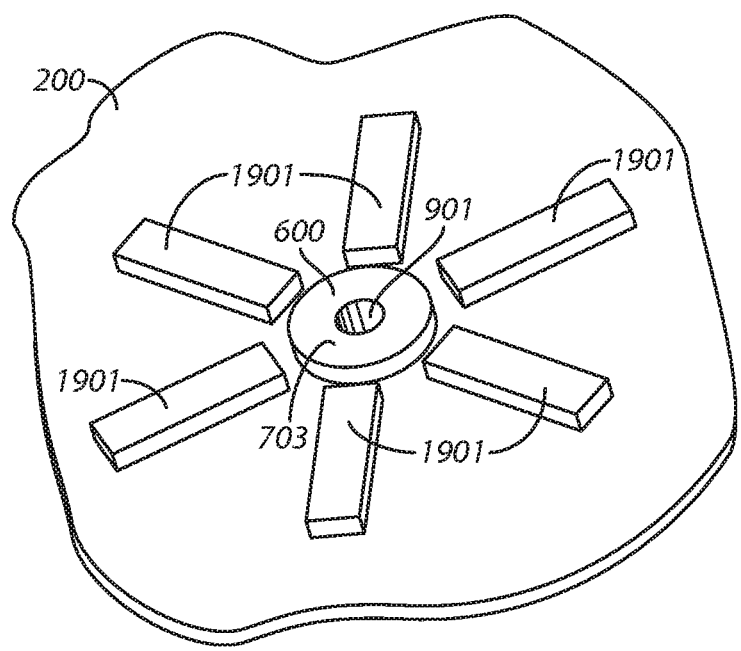
FIG. 19 comprises a perspective detail view as configured in accordance with various embodiments of the invention.

In the illustrative example above the spaced 1600 covered the suction-port opening 901 of the suction port 600. These teachings will accommodate other approaches in these regards, however. As one example in these regards, and as shown in FIG. 18, the spacer 1600 can comprise a ring-shaped component 1800 that surrounds the suction-port opening 901. As another example in these regards, and as shown in FIG. 19, the spacer can comprise a plurality of segments 1901 that are disposed about the suction-port opening 901 like spokes about an axle. It will be understood that these examples are for the sake of illustration and are not intended to suggest any particular limitations in these regards.

Figure 20:
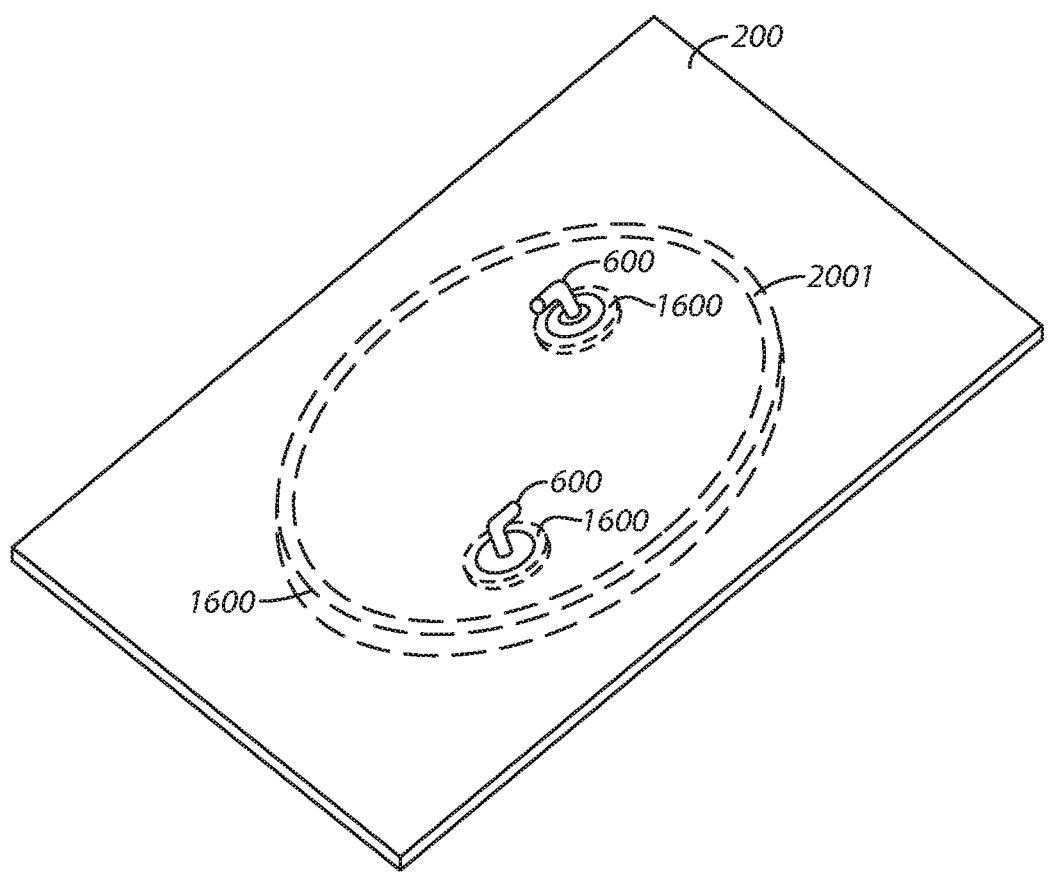
FIG. 20 comprises a perspective view as configured in accordance with various embodiments of the invention.

In the above examples the suction port 600 was located within a fenestration. As yet another example of the flexibility of these teachings, and referring now to FIG. 20, one or more such suction ports 600 can be disposed through a non-fenestrated medical drape 200. In this particular example there are two such suction ports 600 and both have a spacer 1600 as described above associated therewith on a patient side of the medical drape 200 (which is the underside of the medical drape 200 as oriented in FIG. 20).

This illustrative example also includes a spacer 1600 disposed on the patient side of the medical drape 200. In this example the spacer 1600 comprises a ring-shaped component 2001 that surrounds both of the suction ports 600. So configured, a partial vacuum formed between the medical drape 200 and the patient (not shown) within the boundaries of the ring-shaped component 2001 will serve to largely or fully maintain the position of the medical drape 200 with respect to the patient.

And as yet one further example in these regards, the aforementioned incise film 300 can comprise an incise film having an antimicrobial coating disposed thereon. In this case it is possible that the suction formed between the antimicrobial coating and the patient's skin will improve the antimicrobial action of the antimicrobial coating by improving the contact between those two surfaces.

We claim:

1. An apparatus comprising:
   a medical drape having at least one fenestration formed therethrough;
   a pouch disposed about the fenestration to collect at least some of a patient's exuding liquids, wherein the pouch includes a first suction port to facilitate removing at least some of the liquids from the pouch;
   an incise film disposed within the fenestration and having an adhesive disposed on a patient side thereof to facilitate adhering the incise film to a patient;
   a second suction port disposed within the at least one fenestration and through the incise film, such that suction applied to the second suction port further facilitates maintaining the incise film in place on the patient.

2. The apparatus of claim 1 wherein the first suction port comprises a plurality of suction ports disposed and configured to facilitate removing liquids from the pouch.

3. The apparatus of claim 2 wherein the plurality of suction ports substantially surround the fenestration in the medical drape.

4. The apparatus of claim 1 wherein the incise film comprises a pre-fenestrated incise film.

5. The apparatus of claim 1 wherein the second suction port has a first end configured to attach to suction tubing.

6. The apparatus of claim 5 wherein the second suction port includes at least one laterally-disposed suction-input opening configured to be disposed essentially adjacent the patient's skin when the apparatus is operationally disposed on the patient.

7. The apparatus of claim 6 wherein the second suction port includes a plurality of the laterally-disposed suction-input openings.

8. The apparatus of claim 1 wherein the incise film comprises a non-pre-fenestrated incise film.

9. An apparatus comprising:
   a medical drape having at least one fenestration formed therethrough;
   at least one suction port disposed within the at least one fenestration;
   wherein the suction port has a first end configured to attach to suction tubing;
   an incise film disposed at least partially within the fenestration; and
   at least one compressible spacer disposed on a patient side of the medical drape.

10. The apparatus of claim 9 wherein the suction port includes at least one laterally-disposed suction-input opening configured to be disposed essentially adjacent a patient's skin when the medical drape is operationally disposed on the patient.

11. The apparatus of claim 10 wherein the suction port includes a plurality of the laterally-disposed suction-input openings.

12. The apparatus of claim 9 wherein the suction port is disposed through the incise film.

13. The apparatus of claim 12 wherein the incise film has an adhesive disposed on a patient side thereof to adhere the incise film to the patient.

14. The apparatus of claim 9 wherein the spacer is disposed over the at least one suction opening.

\* \* \* \* \*